United States Patent
Maschke et al.

(10) Patent No.: US 7,845,994 B2
(45) Date of Patent: Dec. 7, 2010

(54) LAYOUT OF POWER SEMICONDUCTOR CONTACTS ON A COOLING SURFACE

(75) Inventors: Matthias Maschke, Schwäbisch Hall (DE); Hartmut Schneeweiss, Bad Mergentheim (DE); Anja Ulmer, Blaufelden (DE)

(73) Assignee: EBM-PAPST Mulfingen GmbH & Co. KG, Mulfingen (DE)

( * ) Notice: Subject to any disclaimer, the term of this patent is extended or adjusted under 35 U.S.C. 154(b) by 115 days.

(21) Appl. No.: 12/297,837

(22) PCT Filed: Apr. 4, 2007

(86) PCT No.: PCT/EP2007/053310

§ 371 (c)(1),
(2), (4) Date: Oct. 20, 2008

(87) PCT Pub. No.: WO2007/122084

PCT Pub. Date: Nov. 1, 2007

(65) Prior Publication Data

US 2009/0239424 A1    Sep. 24, 2009

(30) Foreign Application Priority Data

Apr. 20, 2006    (DE) ........................ 10 2006 018 716

(51) Int. Cl.
*H01R 11/11* (2006.01)
(52) U.S. Cl. ........................ 439/883; 439/787
(58) Field of Classification Search ................. 439/786, 439/787, 883–888
See application file for complete search history.

(56) References Cited

U.S. PATENT DOCUMENTS

| 4,707,726 | A | 11/1987 | Tinder |
| 5,274,193 | A | 12/1993 | Bailey et al. |
| 5,466,970 | A | 11/1995 | Smithers |
| 5,909,358 | A | 6/1999 | Bradt |
| 7,056,144 | B2 * | 6/2006 | Barsun et al. ............ 439/362 |
| 7,190,589 | B2 * | 3/2007 | Caines et al. ............ 361/707 |

FOREIGN PATENT DOCUMENTS

| DE | 3612862 | 11/1986 |
| DE | 9213671 | 1/1993 |
| DE | 19543260 | 5/1997 |
| DE | 20014739 | 1/2001 |
| DE | 103 17 182 | 11/2004 |
| EP | 0 788 155 | 8/1997 |
| EP | 1 130 744 | 9/2001 |
| FR | 2 780 456 | 12/1999 |

* cited by examiner

*Primary Examiner*—Khiem Nguyen
(74) *Attorney, Agent, or Firm*—Brinks Hofer Gilson & Lione

(57) ABSTRACT

An arrangement for contact-connecting at least one electronic component mounted in a housing with connection wires to a cooling surface and a spring element that can be fixed in the housing and has at least one spring arm which presses the component against the cooling surface in a contact-pressure position of the spring element is presented. The arrangement is characterized in that the spring element can be inserted into the housing without touching the component, and the housing is provided with retaining means for the spring element adapted in a manner so that no shear forces are produced in the longitudinal direction of the connection wires when the spring element is mounted.

14 Claims, 5 Drawing Sheets

LAYOUT OF POWER SEMICONDUCTOR CONTACTS ON A COOLING SURFACE

FIELD

The present invention relates generally to an arrangement for contact-connecting at least one electronic component. More specifically this invention relates to a power semiconductor, which is mounted in a housing with connection wires, to a cooling surface and a spring element, and can be fixed in the housing and has at least one spring arm that presses the component against the cooling surface in a contact-pressure position of the spring element.

BACKGROUND

In order to ensure power semiconductors are cooled, the semiconductors are placed in thermally conductive contact with a heat sink. In cost-effective embodiments, this is usually realized with springs which press the semiconductor component against the heat sink.

An arrangement of this type is described in German utility model G 92 13 671.0. By virtue of a retaining spring element being pre-mounted in a housing part, the components to be cooled are pressed against an inner wall of the heat sink by spring tongues of the retaining spring when the housing parts are subsequently assembled.

In a similar way, U.S. Pat. No. 5,274,193, German laid-open specification 36 12 862 A1, German patent specification 195 43 260 C2 and German utility model DE 200 14 739 U1 describe spring elements which are clamped between power semiconductors and a housing. The difference in each case is the way in which the spring elements are supported on or fixed to the housing. For example, the spring element may be retained itself by recesses and webs of the housing or by means of additional fixing elements such as screws or clamping rails.

Some retaining apparatuses have a substantially U- or L-shaped spring clip that is placed ("clipped") over a heat sink wall and at the same time over the component and in this way ensures the contact-pressure force between the bearing faces of the heat sink and of the component.

In all apparatuses without additional fixing elements, such as German utility model G 92 13 671.0, the problem arises of the component and the solder point being subjected to shear stresses. This can lead to damage to the component or the solder connection. The shear stresses are produced by forces which act on the component when the apparatus is assembled in a plane parallel to the cooling system surface of the components or the heat sink. Therefore, for example in G 92 13 671.0, the upper housing part is placed on the lower housing part from above by way of a snap-in retaining spring and in the process, the spring is guided along the perpendicular component, as a result of which a force acts in the direction of or in the opposite direction to the connection wires. The spring element may also be likewise inserted parallel to the bearing face of the component as per DE 195 43 260 C2 by means of being pressed in the opposite direction to the connection wires. Although in U.S. Pat. No. 5,274,193, no shear force acts on the components, the retaining spring has to be fixed and the retaining force of the spring element has to be generated by an additional clamping rail.

SUMMARY

The present invention provides an arrangement of the type described in the introduction which, with simple mounting, does not exert any shear forces on the electrical components in the direction of or in the opposite direction to the connection wires.

This is achieved, according to one embodiment of the invention, in that the spring element can be inserted into the housing without touching the component. The housing is provided with retaining means for the spring element in such a way that no shear forces are produced in the longitudinal direction of the connection wires when the spring element is mounted. The spring element can therefore initially be easily inserted into the housing without a great expenditure of force and be positioned in a first mounting position in front of the component.

The insertion grooves are arranged on the housing in such a way that the spring element can be inserted into the housing parallel to the cooling surface without touching the components. The power semiconductor component advantageously remains unaffected by shear forces in the direction of or in the opposite direction to the connection wires during the insertion process.

The retaining means are in the form of latching grooves and permit the spring element to be expediently automatically latched-in in a predefined position. Complicated alignment of the spring element is dispensed with.

The insertion grooves and the latching grooves are arranged on the housing in such a way that the spring element can be moved from the first mounting position to the contact-pressure position by means of a force acting perpendicular to the cooling surface. Even in this second mounting step, no shear force acts in the longitudinal direction of the connection wires; instead the spring element is expediently fixed in the contact-pressure position, from the first mounting position, by forces which act substantially perpendicularly on the cooling surface.

In another embodiment of the present invention, the spring element comprises spring arms which run parallel to one another and are fixed perpendicularly on a support element that connects the two lateral projections of the spring element to one another. On account of the rigidity, this embodiment permits high contact-pressure forces to be applied, with only one spring element advantageously being required for all the semiconductor components that are arranged in a uniform manner.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
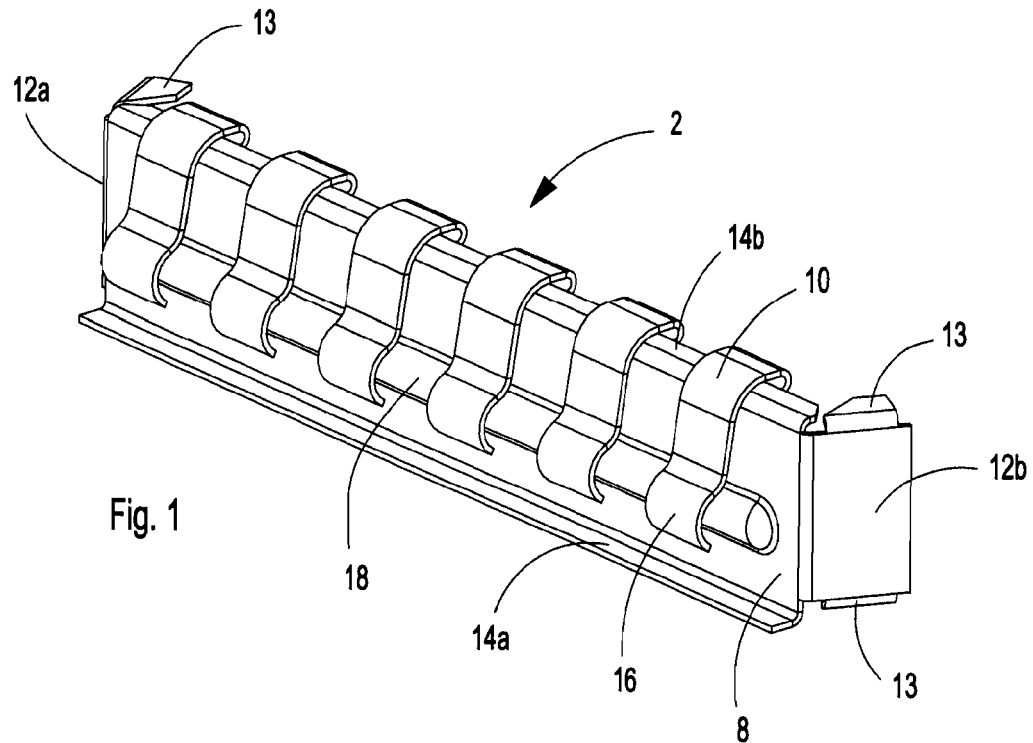
FIG. 1 shows a front view of a spring element according to one aspect of the present invention.

The following description is merely exemplary in nature and is in no way intended to limit the present disclosure or its application or uses. It should be understood that throughout the description and drawings, corresponding reference numerals indicate like or corresponding parts and features.

Figure 2:
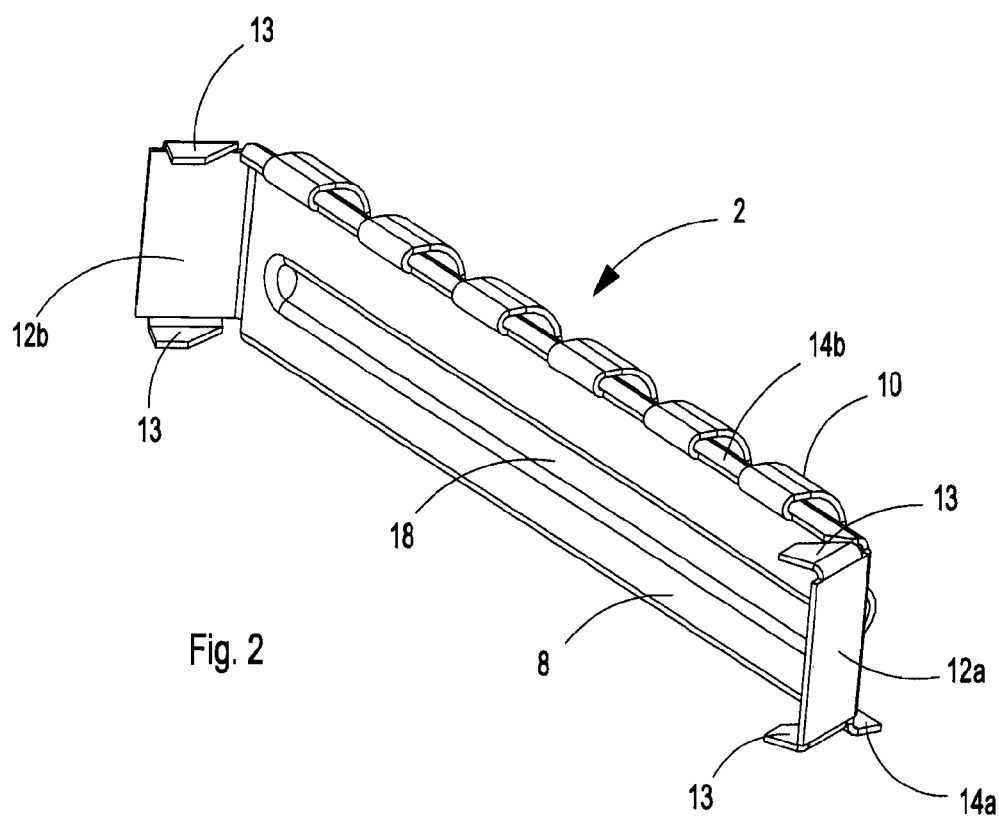
FIG. 2 shows a rear view of the spring element according to one aspect of the present invention.

FIGS. 1 and 2 shows a spring element 2 according to one aspect of the present invention that is intended to be installed in an electronics housing 4 of an electric motor. The spring element 2 comprises a support element 8 that has integrally formed on its upper edge, six spring arms 10 and which has two angled-away projections 12a, 12b on the sides. One skilled in the art will recognize that a support element having a different number of spring arms is feasible. The projections 12a, 12b are formed with lugs 13, which are folded-over inward at a right angle, at the upper and lower edge of the projections, in order to prevent the projections 12a, 12b from buckling. At the upper and lower edge, the support element likewise has narrow sections 14a, 14b which are folded over approximately at a right angle, with the lower section 14a pointing toward the side on which the spring arms 10 are located and the upper section 14b pointing in the opposite direction. Referring to FIG. 2 the upper section 14b continues at equidistant distances and forms the spring arms 10 which run parallel to one another over the upper edge of the support element 8 in a manner bent downward in the direction of the section 14a. At their lower end, the spring arms 10 have a contact region 16 which is curved convexly outward and presses against the components 24 in the contact-pressure position of the spring element 2. A semicircular reinforcing bead 18 that is curved at the front and prevents the spring element 2 from bending runs beneath the center of the support element 8, opposite the contact regions 16, parallel to the upper and lower edge of the support element 8.

Figure 3:
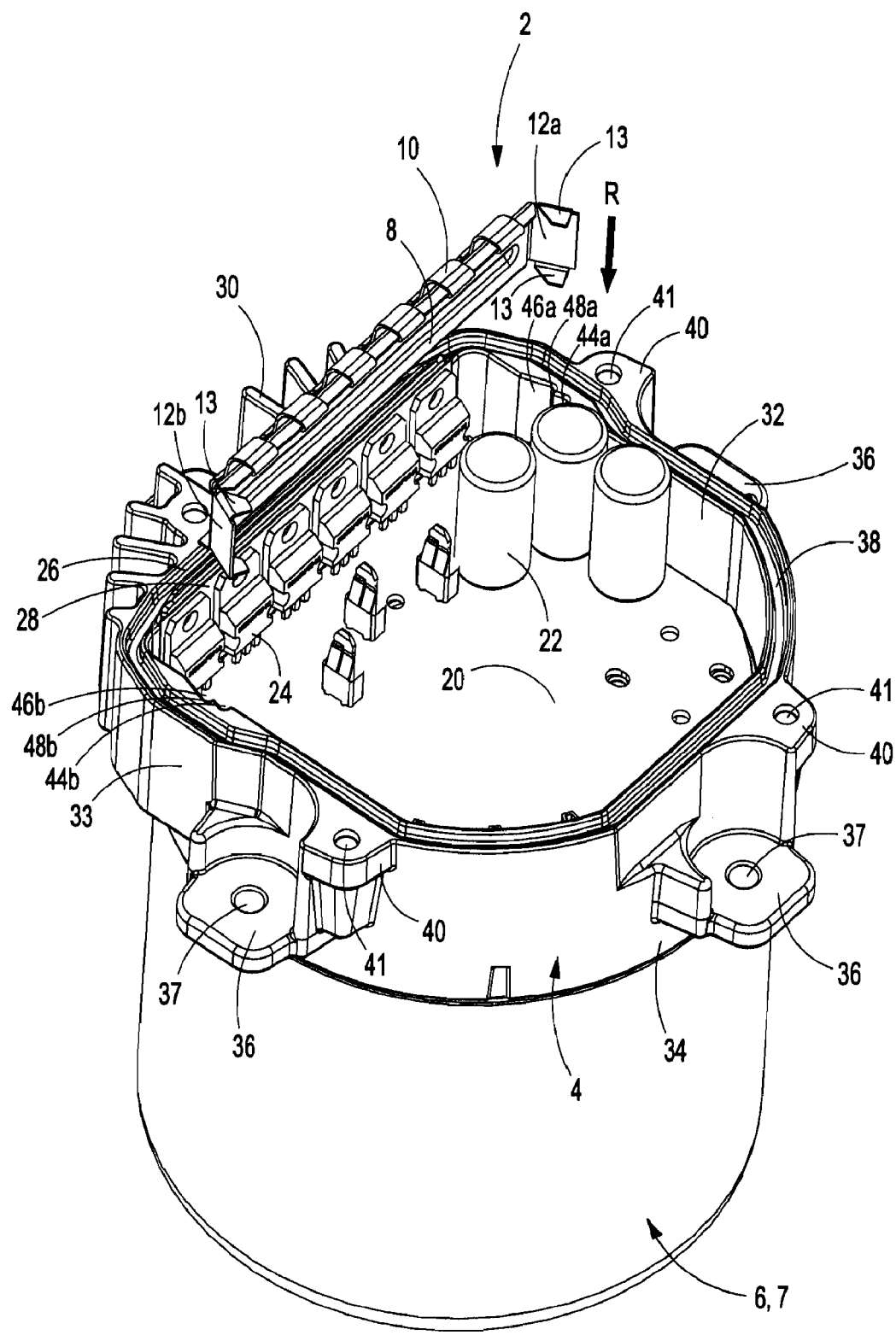
FIG. 3 shows the spring element before it is inserted into an electronics housing.

FIGS. 3 to 7 show a possible variant of the spring element 2 according to another aspect of the invention in an electronics housing 4 of an electric motor 6. Referring to FIG. 3, the electronics housing 4, which accommodates a printed circuit board 20 with electronic components 22 and further electrical connecting elements, is mounted on a rotor housing 7 of the electric motor 6. The electronics housing 4 substantially comprises a circumferential wall that is formed by a flat side wall 26, which acts as a cooling surface, adjoining side walls 32, 33, and a wall 34 that is opposite the flat side wall 26. Mounts 36 with holes 37 for fixing of the housing are integrally formed on the side walls 32, 33 and on the opposite wall 34. The electronics housing 4 can be closed by a housing cover (not illustrated) which engages in a circumferential groove 38 on the end face of the side walls 26, 32, 33, 34. The housing cover is fixed to retaining protrusions 40 which have holes 41. A printed circuit board 20 that is fitted with the electronic components 22, 24 is seated on the base of the electronics housing 4. In one embodiment, power semiconductors 24 are soldered-in on the printed circuit board 20 such that they can be arranged in the interior of the electronics housing 4 on a flat side wall 26 of the electronics housing 4. A thermally conductive electrical insulation layer 28 is inserted between the power semiconductor 24 and the flat side wall 26 in order to permit and to improve the transportation of heat to the side wall 26 that is provided with cooling ribs 30.

Figure 4:
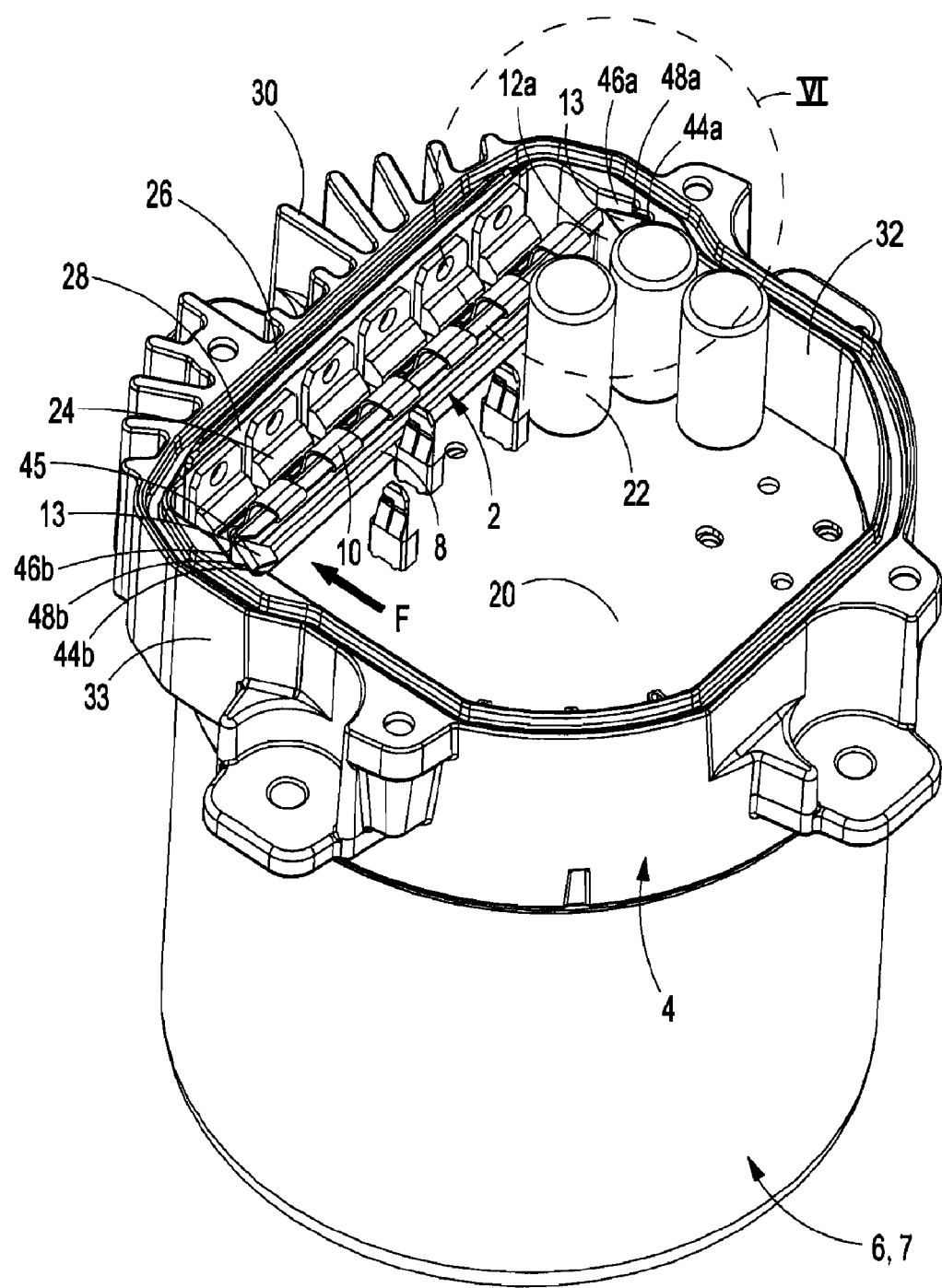
FIG. 4 shows the spring element in a first mounting position.
Figure 6:
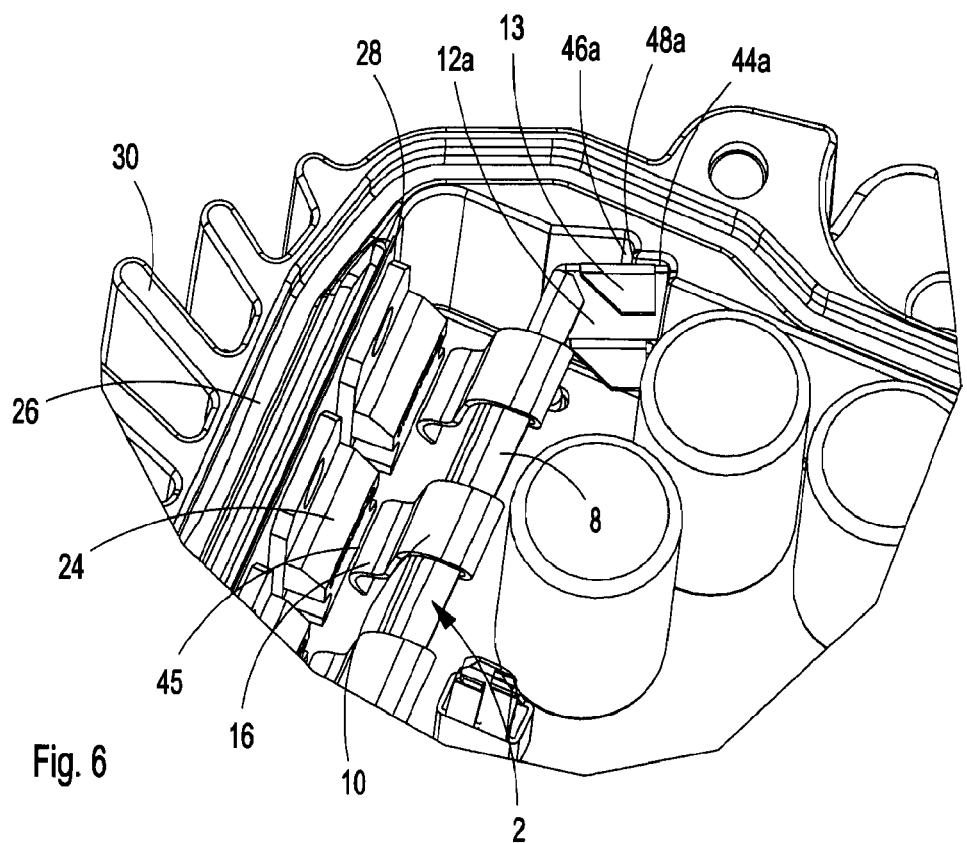
FIG. 6 shows a detailed view of the spring element in the first mounting position.

Groove pairs which run perpendicularly downward and fulfill the function of insertion grooves 44a, 44b and latching grooves 46a, 46b are made in the side walls 32 and 33 that adjoin the flat side wall 26. The two insertion grooves 44a, 44b are located on both sides of the flat side wall 26 in each case at about the same distance from said flat side wall opposite one another in the side walls 32, 33. The spring element 2 is axially inserted into these insertion grooves 44a, 44b in accordance with arrow direction R shown in FIG. 3 and assumes a first mounting position (insertion position). The lugs 13 which are fitted on the upper face may serve as application areas for the insertion forces that are applied manually. In addition to this function as a mounting aid, the upper lug pair 13 also has an additional task: when the spring element 2 is inserted into the electronics housing 4 but is not yet latched, a housing cover cannot be mounted since pins which are injection-molded on the housing cover would then rest on the upper lugs 13 and closing of the cover would be prevented. When the spring element 2 is correctly latched, the pin of the cover can engage in the cleared space and the cover can be mounted. As a result, it is possible to monitor whether the spring element 2 has been correctly mounted. The insertion position is illustrated in FIG. 4. FIG. 6 shows a detailed view of the position of the spring element in this insertion position. It can be seen that the projection 12a is fixed by its end region resting in the insertion groove 44a. When the insertion process is performed, the spring arms 10 do not yet come into contact with the power semiconductors 24, and therefore do not exert any shear forces on the component 24 and its solder point. An air gap 45 remains between the spring arms 10 and the power semiconductors 24.

Figure 5:
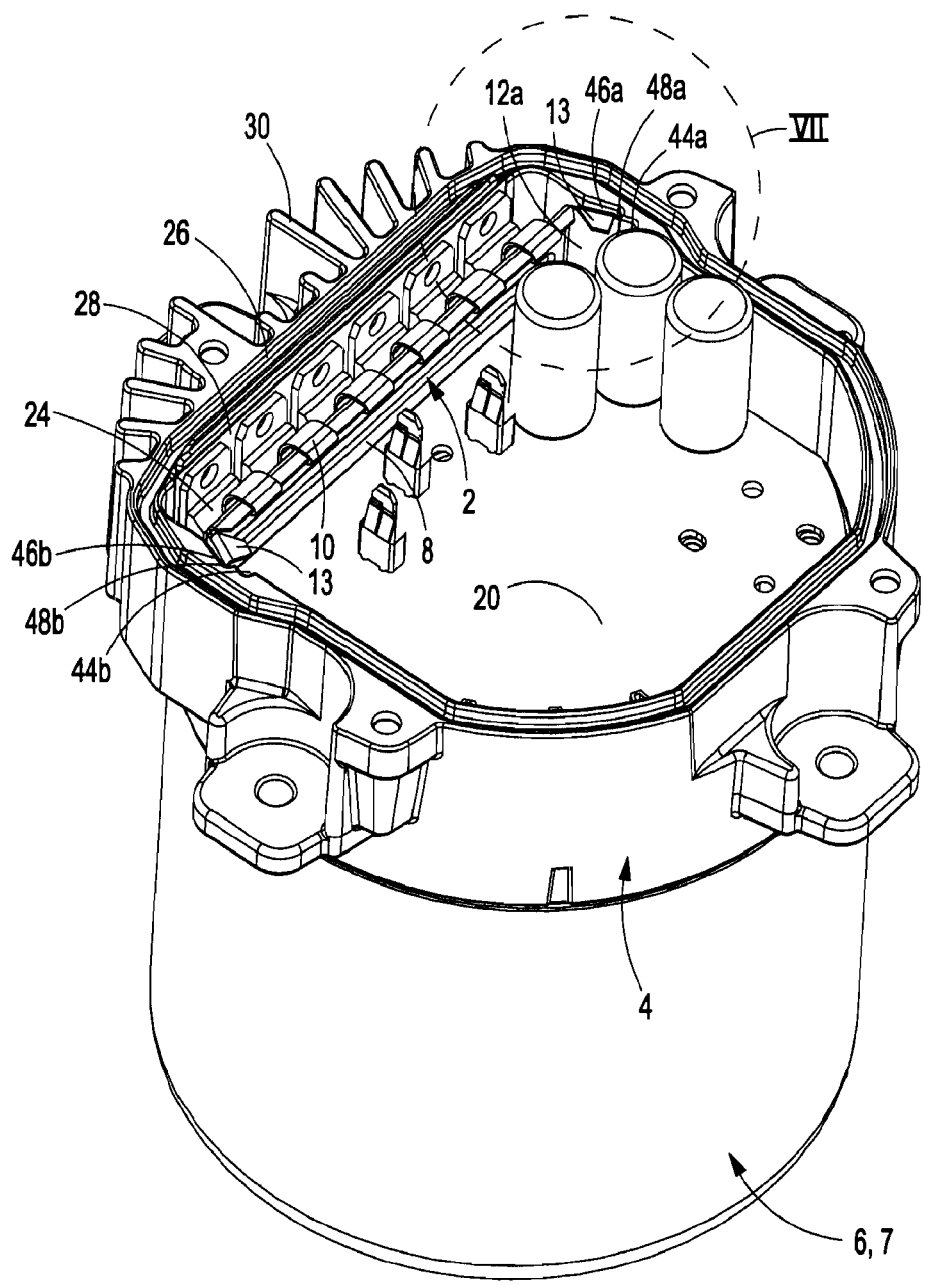
FIG. 5 shows the spring element in a latched-in contact-pressure position.

The latching groove pair 46a, 46b adjoins the insertion grooves 44a, 44b and is made in the same way, but at a shorter distance from the flat side wall 26. The transition region 48a, 48b between the insertion groove 44a (44b) and the latching grove 46a (46b) is formed in such a way that its resistance can be overcome by a force effect F on the spring element 2 perpendicular to the cooling surface as shown in FIG. 4. Referring to FIG. 5, the elastic side projections 12a, 12b are briefly compressed by the transition regions 48a, 48b during the forward movement in the direction of the power semiconductor 24, before they rest in the latching grooves 46a, 46b in the contact-pressure position.

Figure 7:
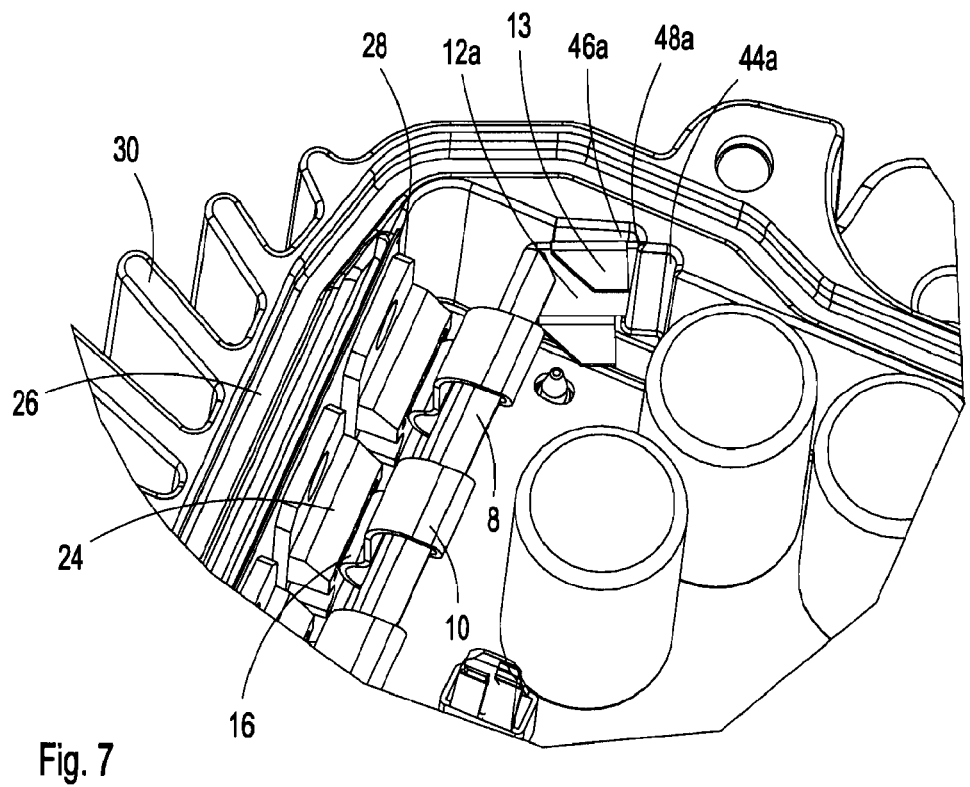
FIG. 7 shows a detailed view of the spring element in a latched-in contact-pressure position.

FIG. 7 shows a detailed view of the position of the spring element 2 on the side wall 32 in the contact-pressure position. The perpendicular edge, which is now embedded in the latching groove 46a, of the end region of the projection 12a fixes the spring element 2. In this contact-pressure position, the spring arms 10 now press on the power semiconductors 24 which as a result are pressed against the thermally conductive insulating layer 28 and thus against the side wall 26, which is in the form of a cooling surface 27. This ensures reliable heat dissipation without the use of further connecting elements, such as screws or clamps. The component 24 and the solder point are not subject to shear forces.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An arrangement for contact-connecting at least one electronic component mounted in a housing with connection wires to a cooling surface comprising a spring element that can be fixed in the housing and has at least one spring arm which presses the component against the cooling surface in a contact-pressure position of the spring element, wherein the spring element can be inserted into the housing without touching the component, and the housing is provided with retaining means for the spring element adapted in a manner so that no shear forces are produced in the longitudinal direction of the connection wires when the spring element is mounted, wherein insertion grooves are arranged on the housing in such a way that the spring element can be inserted into the insertion grooves of the housing in a first mounting position parallel to the cooling surface without touching the component by being guided in the insertion grooves, wherein the retaining means are in the form of latching grooves which retain the spring element in the contact-pressure position, and wherein the insertion grooves and the latching grooves are arranged adjoining each other on the housing and a transition region between the insertion grooves and the latching grooves is formed in such a way that the spring element can be moved from the insertion grooves in the first mounting position into the latching grooves in the contact-pressure position by overcoming a latching spring force F by means of a pushing movement in a direction perpendicular to the cooling surface.

2. The arrangement as claimed in claim 1, wherein the spring element has a support element with two projections that angle away at the sides.

3. The arrangement as claimed in claim 1, further characterized by having spring arms that are fixed so as to run parallel to one another on that edge of the support element which is averted from the printed circuit board in the mounted state.

4. The arrangement as claimed in claim 1, wherein the support element has a reinforcing bead that runs between the two lateral projections.

5. The arrangement as claimed in claim 1, wherein the support element has sections which are folded over at right angles on its longitudinal sides.

6. The arrangement as claimed in claim 2, wherein the lateral projections of the spring element have lugs that are integrally formed at right angles.

7. The arrangement as claimed in claim 1, wherein a spring element is used for all components that are arranged in a row with the same orientation.

8. The arrangement as claimed in claim 1, wherein a lateral wall of the housing is in the form of a cooling surface which has a plane-parallel bearing surface, that points into the interior of the housing, and is provided on its outer face with cooling ribs.

9. The arrangement as claimed in claim 1, wherein a thermally conductive insulating layer is fitted between the cooling surface and the component.

10. A spring element for use in an arrangement as claimed in claim 1, characterized by a support element having two projections that angle away at the sides.

11. An electronics housing for use in an arrangement as claimed in claim 1, characterized by the insertion grooves and the latching grooves arranged on the housing so that the spring element can be moved from the first mounting position to the contact-pressure position by means of the pushing movement in the direction perpendicular to the cooling surface.

12. The arrangement as claimed in claim 1, wherein the electronic component is a power semiconductor.

13. The spring element as claimed in claim 10, further characterized by having spring arms that are fixed so as to run parallel to one another on that edge of the support element which is averted from the printed circuit board in the mounted state.

14. The electronics housing as claimed in claim 11, further characterized by a lateral wall of the housing being in the form of a cooling surface which has a plane-parallel bearing surface that points into the interior of the housing, and is provided on its outer face with cooling ribs.

* * * * *